United States Patent
Kawashima et al.

[11] Patent Number: 5,095,005
[45] Date of Patent: Mar. 10, 1992

[54] POLYPEPTIDE AND ANTIBACTERIAL PREPARATIONS CONTAINING THE SAME

[75] Inventors: Takuji Kawashima, Kawasaki; Kunpei Kobayashi, Yokohama; Tomoko Yaeshima; Suguru Fujiwara, both of Tokyo, all of Japan

[73] Assignee: Morinaga Milk Industry Co., Ltd., Tokyo, Japan

[21] Appl. No.: 503,926

[22] Filed: Apr. 4, 1990

[30] Foreign Application Priority Data

Apr. 7, 1989 [JP] Japan .................... 1-89100

[51] Int. Cl.$^5$ .......................... C07K 7/10; C07K 3/02; A61K 37/02; A23L 3/3463
[52] U.S. Cl. .................................... 514/12; 530/324; 530/858; 426/532
[58] Field of Search ................. 514/12; 530/324, 858; 426/532

[56] References Cited

U.S. PATENT DOCUMENTS 5,008,371 4/1991 Natori .................. 530/858

FOREIGN PATENT DOCUMENTS 1921628 11/1970 Fed. Rep. of Germany .
1012121 12/1965 United Kingdom .

OTHER PUBLICATIONS

Kh. N. Muratova et al., *Eksp. Khir. Anesteziol.*, 12:52-4, (1967), as abstracted in *Chemical Abstracts*, 67:2941, (1962), Abstract #31309v.

Primary Examiner—Jeffrey E. Russel
Assistant Examiner—Stephen Walsh
Attorney, Agent, or Firm—Oblon, Spivak, McClelland, Maier & Neustadt

[57] ABSTRACT

A new polypeptide originating from royal jelly, having a specific amino acid sequence and heat stability. The polypeptide can bear an ordinary procedure for sterilization by heating, and is useful in antibacterial preparations against Gram-positive bacteria containing an effective concentration of said polypeptide which has the following amino acid sequence:

```
  1    2    3    4    5    6    7    8    9
NH2—Val—Thr—Cys—Asp—Leu—Leu—Ser—Phe—Lys—

10   11   12   13   14   15   16   17   18   19
Gly—Gln—Val—Asn—Asp—Ser—Ala—Cys—Ala—Ala—

20   21   22   23   24   25   26   27   28   29
Asn—Cys—Leu—Ser—Leu—Gly—Lys—Ala—Gly—Gly—

30   31   32   33   34   35   36   37   38   39
His—Cys—Glu—Lys—Gly—Val—Cys—Ile—Cys—Arg—

40   41   42   43   44   45   46   47   48   49
Lys—Thr—Ser—Phe—Lys—Asp—Leu—Trp—Asp—Lys—

50   51
Tyr—Phe—COOH.
```

4 Claims, 3 Drawing Sheets

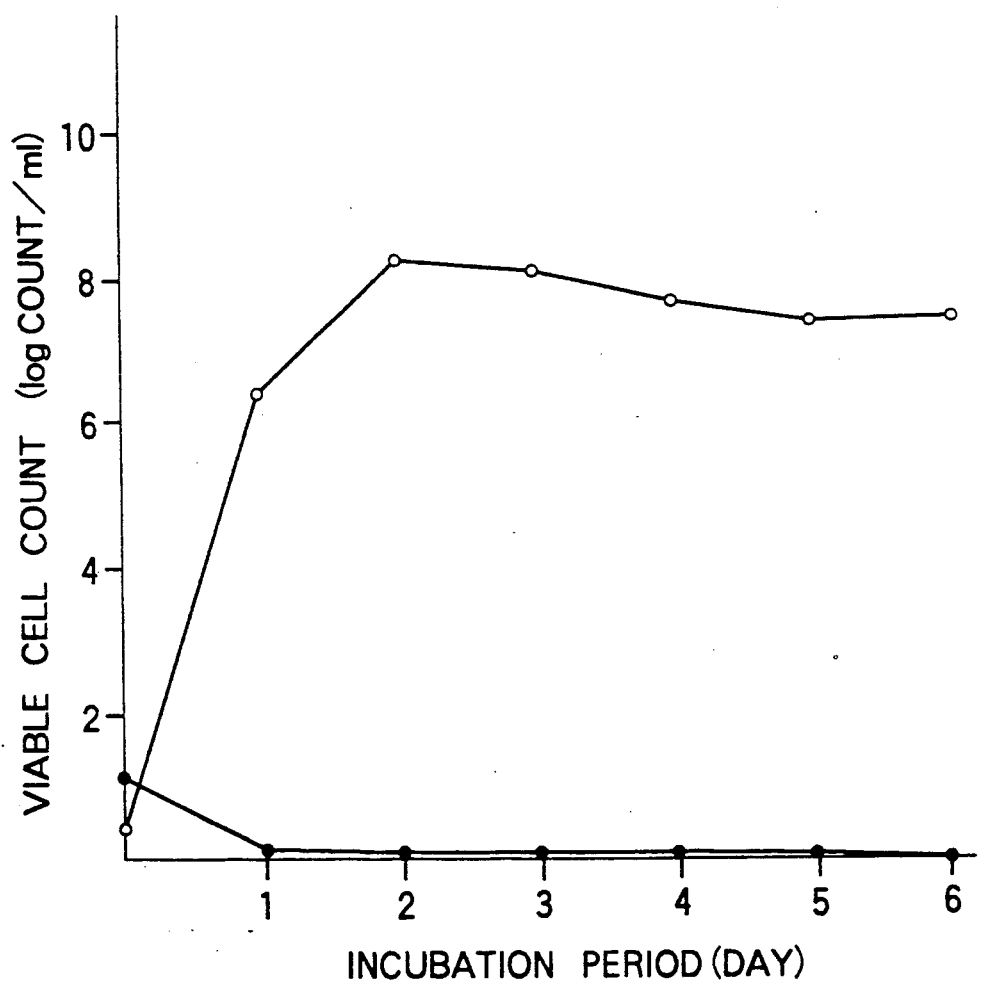

POLYPEPTIDE AND ANTIBACTERIAL PREPARATIONS CONTAINING THE SAME

FIELD OF THE INVENTION

The present invention relates to a new polypeptide having a specific amino acid sequence and antibacterial preparations containing the same.

BACKGROUND OF THE INVENTION

In recent years, bacteriological safety in the food industry has been improved by the technical development of sterilization and sterile packaging. It is, however, still the practice to package processed foods in an ordinary environment (non-sterile atmosphere) with or without sterilization of the processed foods before and after packaging.

DISCUSSION OF THE PRIOR ART

When processed foods are packaged in a non-sterile environment without sterilization, it is possible that the packaged products are contaminated with bacteria, and that the bacterially contaminated foods are deteriorated quickly during storage and transportation thereof. In order to eliminate the deterioration problems, it is necessary to add one or more antiseptics to inhibit proliferation of microorganisms in the packaged foods.

However, most of the antiseptics which have been hitherto utilized may cause undesirable influences on the human body, and hence developments of safer antiseptics have been required.

SOLUTION OF THE PROBLEMS

In view of the present status of the art the, inventors of the present application have conducted research to find safe antibacterial substances among a number of natural materials, and as a result found a potent antibacterial substance in royal jelly. Having isolated, purified and analyzed the substance, it was found that the effective substance is a new polypeptide having a specific amino acid sequence which, so far, has not been reported. The present invention is based on this discovery.

The new substance has excellent heat stability and can be advantageously applied to those foods which are sterilized by heating after packaging.

SUMMARY OF THE INVENTION

It is therefore an object of the present invention to provide a new polypeptide having a specific amino acid sequence.

It is a further object of the present invention to provide antibacterial preparations, which are safely taken by human beings, which contain the new polypeptide as the effective compound, and which are effective especially against Gram-positive bacteria.

It is a still further object of the present invention to provide antibacterial preparations which are bearable to ordinary sterilization by heating, and which are well suited to be added to those foods which are to be subjected to ordinary sterilization by heating after they are packaged.

BRIEF DESCRIPTION OF THE DRAWINGS

FIG. 3 shows bacterial growth inhibition by royal jelly antibacterial polypeptide.

DETAILED DESCRIPTION OF THE INVENTION

The new substance of the present invention is a polypeptide having the amino acid sequence shown hereunder.

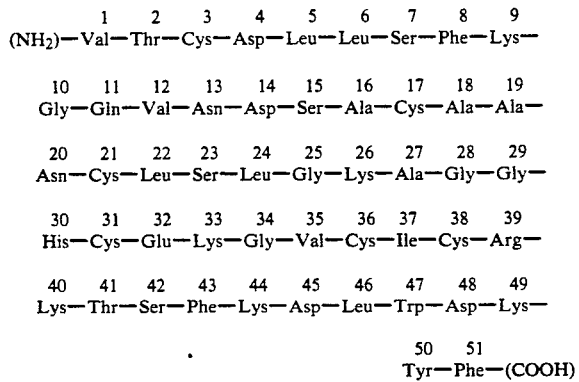

(wherein three intramolecular disulfide linkages were present at positions between 3 and 31, 17 and 36, and 21 and 38.)

The antibacterial properties against Gram-positive bacteria in accordance with the present invention comprise the polypeptide as the active substance.

The polypeptide of the present invention shows excellent antibacterial activity against Gram-positive bacteria. Furthermore, the antibacterial preparations of the present invention containing the polypeptide show excellent antiseptic efficacy when added to processed foods, and advantageously the preparations may keep the antibacterial activity even if the processed foods are subjected to sterilization by heating.

Certainly, the polypeptide by itself can be utilized as an antiseptic compound as it is. It should be noted that the polypeptide and the antibacterial preparations containing the same can be applied to fresh foods to eliminate or minimize the deterioration problem, since sterilization of fresh foods may diminish, degrade and/or deteriorate the freshness, appearance or palatability of the foods.

Now some exemplary tests will be described hereunder for better understanding of the present invention.

TEST 1

[Isolation and Purification of the Polypeptide]

(1-1) Purification of the Polypeptide (1st Stage)

Figure 1:
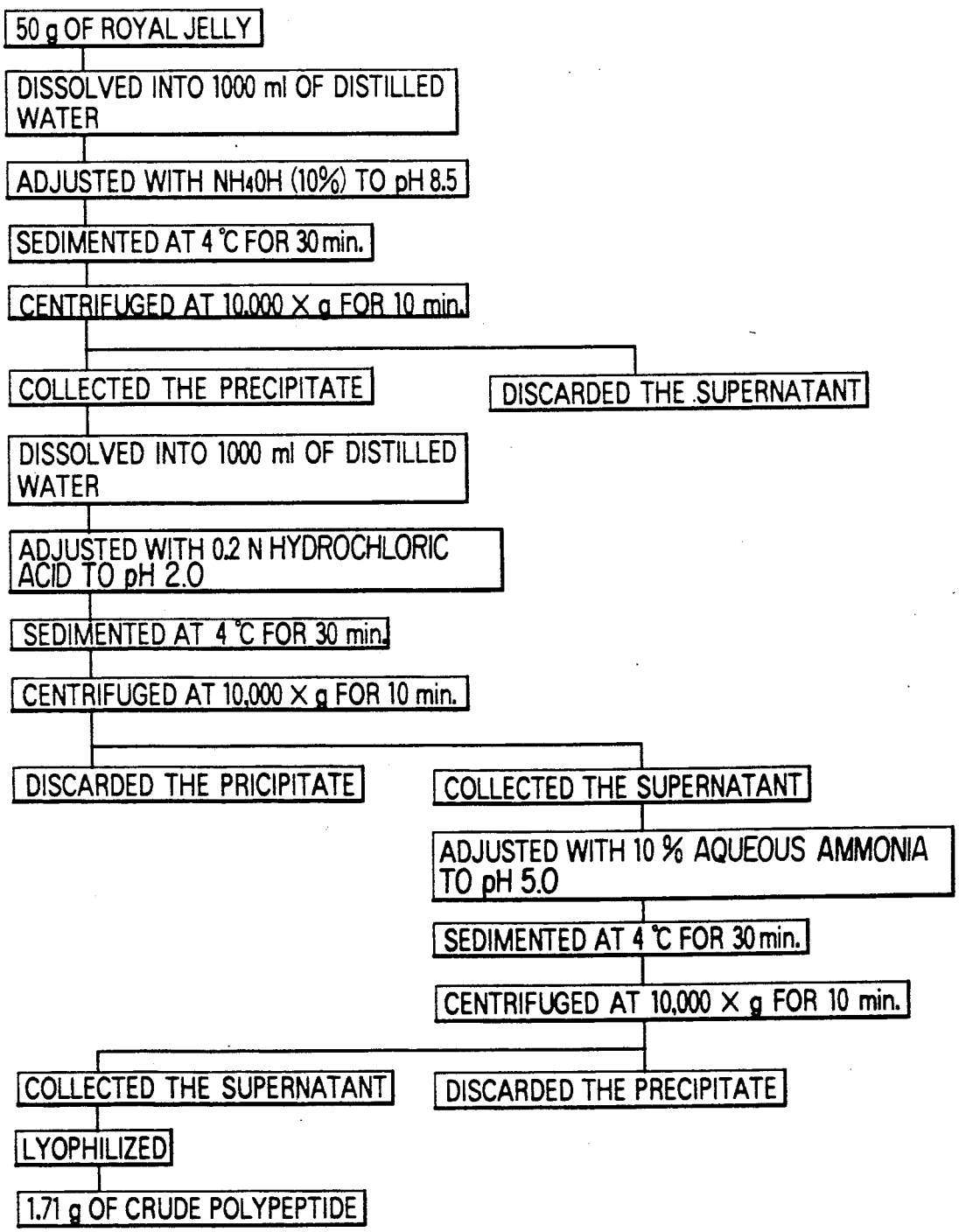
FIG. 1 is a flow chart for the purification of antibacterial polypeptide from royal jelly.

About 1.71 g of crude substance was obtained from 50 g of royal jelly according to the process as shown in FIG. 1 and set forth in the first half of Example 1.

Dissolving 1 g of the resultant crude substance into 20 ml of 10 mM ammonium phosphate buffer solution, pH 4.8, containing 20 mM sodium chloride, the resultant solution was applied to a gel filtration column of Sephadex G-100 (2.6 cm in diameter×90 cm in length; pharamcia, Uppsala, Sweden). The column was then eluted at a flow rate of about 180 ml/hr using the same buffer solution. Ten ml of each fraction was collected.

Aliquots of each fractions (0.5 ml) were assayed for growth inhibitory activity against Lactobacillus helveticus ss jugurti as the index of antibacterial activity. The pattern of peptide elution was monitored at 254 nm by a spectrophotometer (JASCO Tokyo, Japan).

Figure 2:
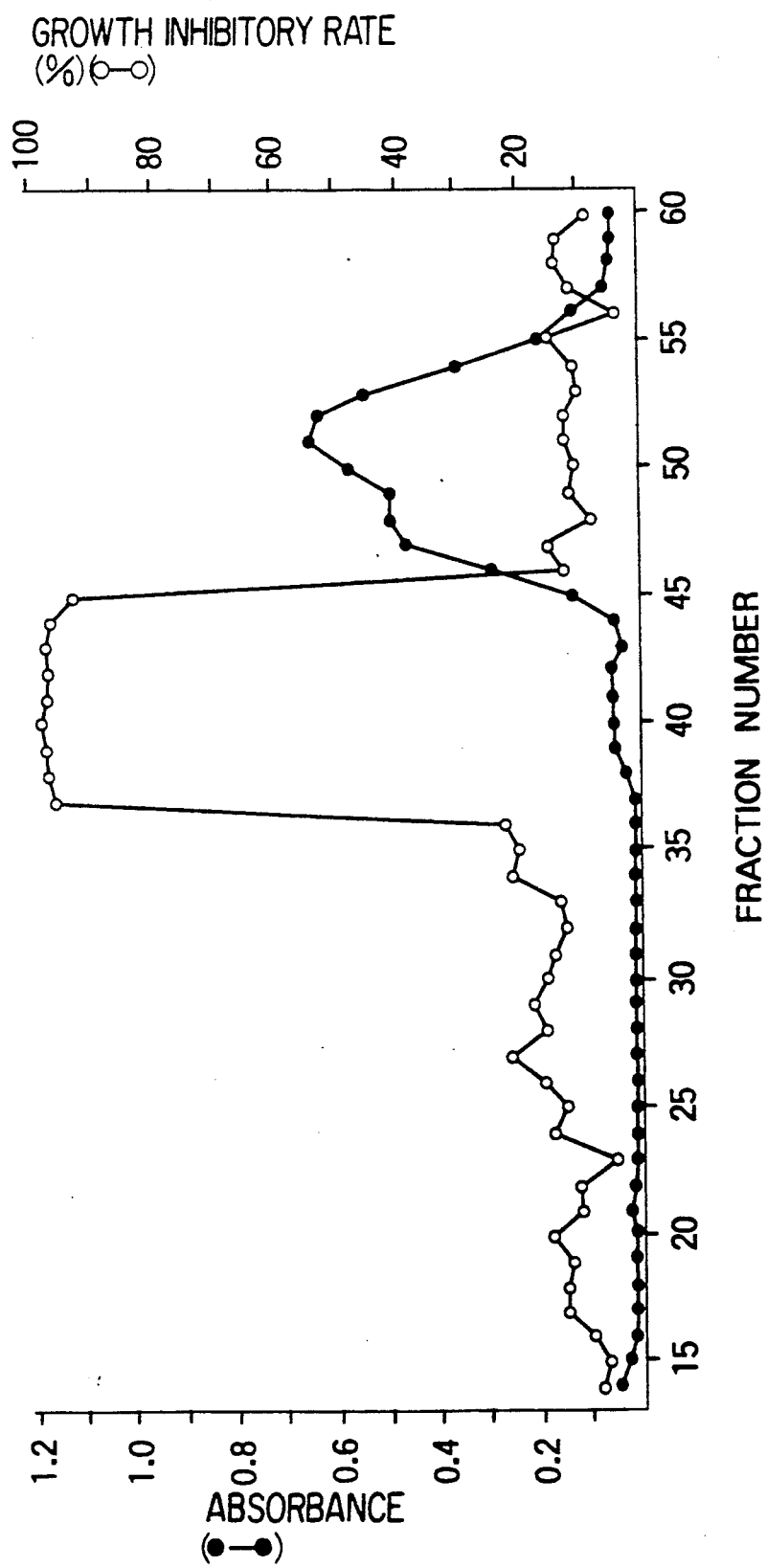
FIG. 2 is a chromatogram showing antibacterial polypeptide purification on Sephadex ® G-100.

The results are shown in FIG. 2. In FIG. 2, absorption (● — ●, left) and growth inhibition rate of bacteria (○—○, right) were plotted as a function of fraction numbers.

From the results, it was confirmed that antibacterial activity was found in the fractions of Ve 380–430 ml, and that the peak of antibacterial activity did not coincide with that of maximum elution of protein.

The fractions found to contain antibacterial activity (Ve 380–430 ml) were pooled and the mixture thereof was dialyzed against distilled water, then lyophilized, thereby obtained 11.7 mg of the crude polypeptide. The yield of the substance at this stage was about 0.04% of the royal jelly.

(1-2) Purification of the Polypeptide (2nd Stage)

Ten mg of the crude polypeptide obtained in step (1-1) of Test 1 was dissolved into 0.1 ml of distilled water and applied to a reverse-phase HPLC column of aquapare RP-300 (type C8, 4.6 mm in diameter×100 mm in length) which was equilibrated previously with 0.1% (V/V) aqueous solution of trifluoro acetic acid. The column was eluted at a flow rate of 0.7 ml/min with a linear gradient of 15–35% (V/V) solvent B (90% (V/V) acetonitrile containing 0.05% (V/V) tri fluoro acetate) in solvent A (0.05% (V/V) trifluoroacetate). The elution of protein from the column was monitored by measuring the absorbance at 220 nm using a Unidec-100V1 spectrophotometer (JASCO, Tokyo, Japan).

Samples were collected at an appropriate interval, antibacterial activity of the collected fractions were determined by the growth inhibition against Lactobacillus helveticus ss jugurti according to the same method as set forth in Test 3.

As the results, it was confirmed that a single well-defined peak of the antibacterial activity was observed in the fraction eluted at 32% acetonitrile (V/V), and the fraction demonstrated the potent antibacterial activity.

The fraction having the potent activity was collected, then lyophilized, yielded 9 mg of purified polypeptide.

TEST 2

[Determination of Amino Acid Sequence]

(2-1) Analysis of Gaseous Phase Protein Sequencer

The purified substance obtained in step (1-2) of Test 1 (hereinafter simply referred to as "the sample" in this Test) was subjected to gaseous phase Model 470A protein sequencer (Applied Biosystems Inc., Foster City, CA, U.S.A.). The resultant PTH amino acids were analyzed by PTH analyzer Model 120A (Applied Biosystems Inc., CA, U.S.A.) in accordance with the routine procedures. Detection of PTH amino acid residues was carried out, comparing retention time of PTH amino acids with the reference PTH amino acids (Wakoh Pure Chemical Ind., Tokyo, Japan).

As the result, it was determined that the amino acid sequence from N-terminus revealed 51 amino acid residues as shown hereunder:

```
      1    2    3   4    5    6    7    8    9
(NH2)—Val—Thr—X—Asp—Leu—Leu—Ser—Phe—Lys—
```

-continued
```
 10   11   12.  13   14   15   16  17   18   19
Gly—Gln—Val—Asn—Asp—Ser—Ala—X—Ala—Ala—

20 21   22   23   24   25   26   27   28   29
Asn—X—Leu—Ser—Leu—Gly—Lys—Ala—Gly—Gly—

30 31   32   33   34   35   36   37   38   39
His—X—Glu—Lys—Gly—Val—Cys—Ile—Cys—Arg—

40   41   42   43   44   45   46   47   48   49
Lys—Thr—Ser—Phe—Lys—Asp—Leu—Trp—Asp—Lys—

50   51
                                    Tyr—Phe—(COOH)
```

In the amino acid sequence shown above, X refers to the amino acids which could not be identified by the gaseous phase protein sequencer (the same shall apply hereinafter).

The abbreviations of amino acids in the sequence data are adopted by the Commitee of Biochemistry (CBN) of IUPAC-IUB, for the sake of precaution, the list of the crossreference thereof is given hereunder.

| Ala: | L-alanine | Arg: | L-arginine |
|---|---|---|---|
| Asn: | L-aspargine | Asp: | L-aspartic acid |
| Cys: | L-cysteine | Gln: | L-glutamine |
| Glu: | L-glutamic acid | Gly: | L-glycine |
| His: | L-histidine | Ile: | L-isoleucine |
| Leu: | L-leucine | Lys: | L-lysine |
| Met: | L-methionine | Phe: | L-phenylalanine |
| Pro: | L-proline | Ser: | L-serine |
| Thr: | L-threonine | Trp: | L-tryptophane |
| Tyr: | Tyrosine | Val: | L-valine |

Since, 4 of 51 amino acid residues were not identified, following test was carried out to determine the unidentified residue of polypeptide.

(2-2) Digestion with Staphylococcus Aureus V8 Protease

The 0.5 mg of the purified protein was dissolved into 0.2 ml of 0.1 M ammonium formate and the resultant solution was incubated at 37° C. for 4 hours with V8 protease (Sigma Chemical Co., St. Louis, MO, U.S.A.) was added to make the enzyme/peptide concentration ratio of 1:50. The resultant reaction mixture was subjected to high performance liquid chromatography in the same manner as in step (1-2) of Test 1. Two peptide fragments of the protein, namely VP1 and VP2 were isolated. Amino acid sequences of VP1 and VP2 were analyzed in the same manner as in step (2-1) of this test. The result was as follows:

VP1:
```
      1    2    3   4    5    6    7    8    9
(NH2)—Val—Thr—X—Asp—Leu—Leu—Ser—Phe—Lys—

10   11   12   13   14   15   16  17   18   19
Gly—Gln—Val—Asn—Asp—Ser—Ala—X—Ala—Ala—

20 21   22   23   24   25   26   27   28   29
Asn—X—Leu—Ser—Leu—Gly—Lys—Ala—Gly—Gly—

30   31   32
                                 His—X—Glu—(COOH)
```

VP2:
```
      33   34   35   36   37   38   39   40   41
(NH2)—Lys—Gly—Val—Cys—Ile—Cys—Arg—Lys—Thr—

42   43   44   45   46   47·  48   49
Ser—Phe—Lys—Asp—Leu—Trp—Asp—Lys—
```

-continued 50  51
     Tyr—Phe—(COOH)

(2-3) Digestion with Lysyl Endopeptidase

The purified protein (1 mg) in 250 ml of 50 mM Tris/HCl (pH 9.0) was incubated at 37° C. for 1 hour with 15 μl lysyl endopeptidase (0.15 U, about 30 μg). The resultant reaction mixture was subjected to reverse-phase high performance liquid chromatography in the same manner as in step (1-2) of Test 1. The column was eluted with linear concentration gradient of acetonitrile solution. Five new peptide peaks having different protein absorption were generated. The respective fractions showing the peptide peaks were named as VP1, VP2, VP3, VP4, and VP5 for convenience. Determination of amino acid sequences of the each peptide was made in the same manner as in step (2-1) of this Test. The results were as follows:

VP1:
           50  51
(NH₂)—Try—Phe—(COOH)

VP2:
           41  42  43  44
(NH₂)—Thr—Ser—Phe—Lys—(OOH)

VP3:
           45  46  47  48  49
(NH₂)—Asp—Leu—Trp—Asp—Lys—(COOH)

VP4:
           27  28  29  30  31  32  33
(NH₂)—Ala—Gly—Gly—His—X—Glu—Lys—(COOH)

1  2  3  4  5
(NH₂)—Val—Thr—X—Asp—Leu—

6  7  8  9
               Leu—Ser—Phe—Lys—(COOH)

VP5:
           34  35  36  37  38  39  40
(NH₂)—Gly—Val—Cys—Ile—Cys—Arg—Lys—(COOH)

10  11  12  13  14  15  16  17  18
(NH₂)—Gly—Gln—Val—Asn—Asp—Ser—Ala—X—Ala—

19  20  21  22  23  24  25  26
       Ala—Asn—X—Leu—Ser—Leu—Gly—Lys—(COOH)

It was also found that the peaks VP4 and VP5 consisted of two peptide fragments.

The unidentifiable amino acid residues in peak VP4 were assigned to be cysteine which was independently verified by analysis of FAB mass spectroscopy.

(2-4) Amino Acid Sequence of Pyridylethylated Peptide Fragments

Peptide fragments VP4 and VP5 obtained in step (2-3) were reduced by addition of 2-mercaptoethanol and were alkylated by addition of 4-vinylpyridine. More particularly, lyophilized peptide fragments VP4 and VP5 (100 μg of each) were dissolved into 50 μl of 0.2N ethylmorpholine acetate buffer, pH 8.0, and was reduced by addition of 1 μl of 2-mercaptoethanol and kept at room temperature for 30 minutes. Subsequently, to each of the resultant solutions, 1 μl of 4-vinylpyridine was added and reacted at room temperature for 30 minutes with stirring for pyridyl ethylation of cysteines or cystines. Each of the resultant peptide fragments were subjected to reverse-phase high performance liquid chromatography in the same manner as in step (1-3) of Test 1 for fractionation. Each of the pyridylethylated peptides was analyzed for primary amino acid sequence in the same manner as in step (2-1) of this Test. As the result, VP4 was separated into two fragments, VP6 and VP7, and VP5 into VP8 and VP9 which had amino acid sequences as follows:

VP6:
           27  28  29  30  31  32  33
(NH₂)—Ala—Gly—Gly—His—PECys—Glu—Lys—(COOH)

VP7:
           1  2  3  4  5
(NH₂)—Val—Thr—PECys—Asp—Leu—

6  7  8  9
               Leu—Ser—Phe—Lys—(COOH)

VP8:
           34  35  36  37  38  39  40
(NH₂)—Gly—Val—PECys—Ile—PECys—Arg—Lys—(COOH)

VP9:
           10  11  12  13  14  15
(NH₂)—Gly—Gln—Val—Asn—Asp—Ser—

16  17  18  19  20  21
     Ala—PECys—Ala—Ala—Asn—PECys—

22  23  24  25  26
      Leu—Ser—Leu—Gly—Lys—(COOH)

The abbreviation "PECys" shown in the above denotes pyridylethylated cysteine.

From the result of the analysis that VP4 peptide fragment was separated into two fragments after reduction, containing pyridylethylated cysteine, it was found that two cysteine residues in the VP4 were linked with disulfide bridges.

It was also found that VP5 peptide fragment had disulfide bridges. This result was verified by digestion of the VP5 with thermolysin. Sequence analysis of proteolytic peptides derived from the purified polypeptide was performed as follows. To 0.05 ml of 0.2N ethylmorpholine acetate, 0.3 mg of the polypeptide was dissolved. The treatment of the polypeptide with 2 μl of thermolysin (25 mg/ml) was carried out at 37° C. for 2 hours. The resultant reaction mixture was directly subjected to reverse-phase high performance liquid chromatography in the same manner as in step (1-3) of Test 1. Two peptides corresponding to (NH₂)-Ala-Ala-Asp-Cys-(COOH) and (NH₂)-Ile-Cys-Arg-Lys-(COOH) were isolated separately implying the presence of disulfide bridge between residues 21 and 38.

From the results, it was concluded that the primary structure of the polypeptide isolated from royal jelly was as follows:

1  2  3  4  5  6  7  8  9
(NH₂)—Val—Thr—Cys—Asp—Leu—Leu—Ser—Phe—Lys—

10  11  12  13  14  15  16  17  18  19
   Gly—Gln—Val—Asn—Asp—Ser—Ala—Cys—Ala—Ala—

20  21  22  23  24  25  26  27  28  29
   Asn—Cys—Leu—Ser—Leu—Gly—Lys—Ala—Gly—Gly—

30  31  32  33  34  35  36  37  38  39
   His—Cys—Glu—Lys—Gly—Val—Cys—Ile—Cys—Arg—

-continued

```
40  41  42  43  44  45  46  47  48  49
Lys—Thr—Ser—Phe—Lys—Asp—Leu—Trp—Asp—Lys—

50  51
                                    Tyr—Phe—(COOH)
```

(three intramolecular disulfide linkages were present at positions between 3 and 31, 17 and 36, and 21 and 38.)

In the belief of the inventors, the polypeptide is a new substance which has not been hitherto reported. The calculated molecular mass of the substance is 5523 Da., having the maximum absorption peak at 268 nm. The substance is quite soluble in water.

It was also found that the antibacterial activity was relatively heat stable since activity was retained after heating for 15 minutes at 100° C. The antibacterial activity at different temperatures and incubation time was determined by growth inhibition against Lactobacillus helveticus ss jugurti in the media of MRS broth (Difco Lab., Detroit, Mich., U.S.A.).

TEST 3

[Test on Anibacterial Activity]

(3-1) Preparation of Bacterial Suspension

The antibacterial effects of the polypeptide were tested against 10 species of Gram-positive and 25 species of Gram-negative bacteria. All cultures were maintained as frozen stocks at −75° C. Before experimental use, cultures were propagated twice at 37° C. in the medium of MRS broth (Difco Lab., Detroit, Mich., U.S.A.). Bacteria in the experimental phase of growth were collected by centrifugation at 1,300×g for 10 minutes and suspended in 10 ml of isotonic saline thereby the respective bacterial suspensions ($10^6$ cells/μl) were prepared.

(3-2) Preparation of Sample Liquid Media

The purified polypeptide which was prepared in the same manner as in step (1-2) of Test 1 was dissolved into MRS broth (Difco Lab., Detroit, Mich., U.S.A.) at different concentrations; 0.01 μM (about 0.05 ppm), 0.1 μM (about 0.5 ppm) and 1 μM (about 5 ppm). The medium was filter-sterilized using a Millex GV filter (pore size: 0.22 μm, Millipore Ltd., Tokyo, Japan) thereby samples to be tested were prepared.

(3-3) Method

To 3 ml of each of the culture media, 90 μl of bacterial suspensions was inoculated. After inoculation at 37° C. for 10 hours, each culture was rapidly chilled and its turbidity was measured at 660 nm and bacterial growth inhibition was calculated as compared with control culture.

The results shown in Table 1 indicate that the polypeptide inhibited the growth (>50%) of Gram-positive bacteria tested including Lactobacillus lactis, L. helveticus, L. bulgaricus, and Leuconostock cremoris at the effective concentration of 0.1 μM. At the concentration of 1 μM, growth inhibitory effect was observed strongly against Clostridium butyricum, Staphylococcus aureus, Corynebacterium, Streptococcus cremoris and Streptococcus thermophilus. It is obvious that the polypeptide of the present invention has an excellent antibacterial activity only against various Gram-positive bacteria. The polypeptide showed, however, no antibacterial activity against the Gram-negative bacteria tested.

TABLE 1

| Gram's staining | bacterial strains | concentration | | |
|---|---|---|---|---|
| | | 0.01 μM | 0.1 μM | 1 μM |
| − | Escherichia coli 1-111 | − | − | − |
| | Escherichia IID 562 | − | − | − |
| | Escherichia IID 5208 | − | − | − |
| − | Salmonella infantis | − | − | − |
| | Salmonella typi-murium | − | − | − |
| | Bacteroides vulgatus | − | − | − |
| | Bacteroides fragilis | − | − | − |
| − | Klebsiclle pneumomiae | − | − | − |
| − | Pseudomonas | − | − | − |
| + | Candida albicans IID 867 | − | − | − |
| − | Campylobacter jejiuni | − | − | − |
| + | Clostridium perfringens ATCC 13124 | − | − | − |
| | Clostridium butiricum | − | − | − |
| + | Eubacterium aerofaciens | − | − | − |
| + | Corynebacterium | − | ± | +++ |
| + | Staphylococcus aureus SCD | ± | ± | +++ |
| + | Lactobacillus helveticus ss jugurti | ± | +++ | +++ |
| | Lactobacillus leichmannii ATCC 7830 | − | +++ | +++ |
| | Lactobacillus helveticus ATCC 8018 | − | +++ | +++ |
| | Lactobacillus bulgaricus ATCC 11841 | ± | +++ | +++ |
| | Lactobacillus lactis ATCC 8000 | + | +++ | +++ |
| | Lactobacillus casei ATCC 393 | − | − | − |
| | Lactobacillus plantarum ATCC 14917 | − | − | − |
| | Lactobacillus delbrueckii IAM 1085 | − | − | − |
| | Lactobacillus fermentum 4061 II-87 | − | − | − |
| | Lactobacillus sarivarius ATCC 11742 | − | − | − |
| | Lactobacillus acidophilus ATCC 341 | − | − | + |
| + | Streptococcus faecalis | − | − | − |
| | Streptococcus cremoris | − | − | +++ |
| | Streptococcus lactis ss diacetilactis | − | − | − |
| | Streptococcus lactis ATCC 19435 | − | − | − |
| | Streptococcus thermophilus ATCC 19258 | − | − | +++ |
| + | Leuconostoc cremoris ATCC 19254 | − | +++ | +++ |
| + | Bacilus cremoris IAM 1073 | − | − | − |
| | Bacillus licheniformis IAM 11054 | − | − | − |

The evaluation criteria in this table is as follows:
−: 0–20%
±: 21–40%
+: 41–60%
++: 61–80%
+++: 81–100%

It will be understood from the result that the polypeptide of the present invention has growth inhibitory activity against Gram-positive bacteria such as Clostridium, Corynebacterium, and Staphyrococcus which are undesirable bacteria in food industry. The polypeptide of the present invention also has growth inhibitory activity against relatively wide range of bacteria including Streptococcus, Lactobacillus and Leuconostoc and hence it can be utilized as an antibacterial compound against excessive fermentation, prevention against putrefaction of pickles or fermented milk products, as well as a preservative against deterioration of such products.

Test 1

[Applications in Food-Processing]

Utility of the polypeptide of the present invention as an antiseptic for foods was tested with respect to antibacterial activity against Streptococcus aureus in soyabean milk.

(4-1) Preparation of Food

To prepare the test food, sterilized soya-bean milk (Morinaga Milk Ind. Co., Tokyo, Japan) was diluted 5-fold. Fifty ml of the diluted soya-bean milk was inoculated at a cell concentration of 100/ml with the Streptococcus aureus FDA 209P suspension in saline which was preliminarily incubated at 37° C. for 24 hours.

(4-2) Preparation of Solution Containing The Polypeptide of the Present Invention To prepare sample solution of the polypeptide, 1 mg of the purified polypeptide prepared in the same manner as in Example 2 was dissolved into 10 ml of distilled water and the solution was filter-sterilized using a Millex GV filter (pore size: 0.22 μm, Millipore Limited, Tokyo, Japan).

(4-3) Potency in Preservation

To 50 ml of the test food prepared in step (4-1), 10 ml of the sample solution of the polypeptide was homogeneously added and the resultant mixture was incubated at 37° C. up to one week in an incubation flask. The concentration of the polypeptide added in the test food was 10 ppm (about 2 μM).

Aliquots of the incubation medium (1 ml) was taken out from the incubation flask at the interval of 24 hours for determination of viable bacterial counts. To count bacteria, the medium was further diluted with saline solution (0.8% sodium chloride), and 1 ml of the resultant solution was incubated for 24 hours on an agar plate (10 ml of standard culture medium).

As control groups, a mixture solution containing the test food and sterilized distilled water instead of the sample solution was prepared and incubated in the same manner as in the test samples. Viable bacterial counts as a function of incubation period are shown in FIG. 3.

As shown in FIG. 3, the viable counts in control group (○—○) reached to $10^8$/ml within two days whereas in the test groups (●—●) bacterial growth was greatly inhibited. This inhibitory effect lasted for one week tested in this study.

Although the experiment was terminated for one week, it is possible that the inhibitory effect on bacterial growth could last longer based on the results shown in FIG. 3. It must be noted that the growth inhibitory activity depends upon the initial viable count of bacteria inoculated, and lesser initial cell counts were resulted in greater growth inhibitory effect.

It is possible that the antibacterial preparation in accordance with the present invention is well applied to those foods which are preliminarily sterilized.

The effective quantity of the polypeptide of the present invention to be added to foods is comparable with the quantity range of royal jelly to be usually taken. Thus, it is considered that there is no undesirable influence to human beings. It will be also understood that the polypeptide isolated and purified according to the present invention can be produced by microorganisms utilizing biotechnology.

EXAMPLE 1

In FIG. 1, 50 g of native royal jelly (Akitaya, Gifu, Japan) from Apis mellifera L. was dissolved in 1000 ml of distilled water and the resultant solution was adjusted with 10% of ammonium hydroxide to pH 8.5. After 30 minutes of sedimentation, the alkaline suspension was centrifuged at 10,000×g for 10 minutes at 4° C. using a SCR-20BB high speed centrifuge (Hitachi, Tokyo, Japan). The precipitate was collected and resuspended in 100 ml distilled water and the pH of the suspension was lowered with 0.2N hydrochloric acid to pH 2.0. After sedimentation at 4° C. for 30 minutes, the suspension was centrifuged at 10,000×g for 10 minutes. The resultant supernatant was collected and adjusted to pH 5.0 with 10% (V/V) ammonium hydroxide. After resedimentation, suspension was recentrifuged at 10,000×g for 10 minutes. The clear supernatant was retained and lyophilized, yielded 1.71 g of crude polypeptide (3% of native royal jelly).

The crude polypeptide (1 g) was dissolved in 20 ml of 10 mM ammonium phosphate buffer, pH 4.8, containing 20 mM sodium chloride and applied to a gel filtration column of Sephadex G-100 (2.6 cm in diameter×90 cm in length, Pharmacia, Uppsala, Sweden), that had been equilibrated previously with the same buffer. The column was then eluted at a flow rate of 20 ml/hour with 10 mM ammonium phosphate buffer, pH 5.0. Theractions of Ve 380-430 ml were collected and dialyzed against distilled water and lyophilized, yielded 11.7 mg of partially purified polypeptide.

The growth inhibitory effect of the partially purified polypeptide was tested against Lactobacillus helveticus ss jugurti. It was observed that the partially purified polypeptide showed the similar effect to that shown in Test 3.

EXAMPLE 2

For further purification by high pressure liquid chromatography, 10 mg of the partially purified substance was dissolved into 0.1 ml of distilled water and applied to a reverse-phase HPLC column of Aquapore RP-300 (type C8, 4.6 in diameter×100 mm in length) connected to a Tri IV HPLC system (JASCO, Tokyo, Japan). The column was eluted at a flow rate of 0.7 ml/min with a linear gradient of 15-35% (V/V) solution BL 90% (V/V acetonitrile containing 0.1% (V/V) trifluoro acetate) in solvent A (0.1% (V/V) trifluoro acetate). The elution of polypeptide from the column was monitored by measuring the absorbance at 220 nm using a Unidec 100 VI spectrophotometer (JASCO, Tokyo, Japan).

In the same manner as in Test 3, antibacterial activity against Lactobacillus helveticus ss jugurti was determined and it was confirmed that the essentially similar results to Test 3 were demonstrated.

EFFECTS OF THE INVENTION

The effects of the invention are as follows:

(1) The polypeptide of the present invention does not have undesirable influence to human beings when taken in conjunction with foods.

(2) Addition of the polypeptide of the present invention to foods at the concentration of 0.1 μM (about 0.5 ppm) and preferably at 1 μM (about 5 ppm) may result almost complete inhibition of proliferation of various Gram-positive bacteria.

(3) The polypeptide of the present invention is stable under an ordinary condition of sterilization by heating. Thus, it can be advantageously utilized to those food which are subjected to sterilization by heating after addition of the polypeptide thereto.

What is claimed is:

1. An antibacterial composition against Gram-positive bacteria comprising an antibacterially effective quantity of the isolated and purified polypeptide having the following amino acid sequence:

```
     1    2    3    4    5    6    7    8    9
NH2—Val—Thr—Cys—Asp—Leu—Leu—Ser—Phe—Lys—

10   11   12   13   14   15   16   17   18   19
    Gly—Gln—Val—Asn—Asp—Ser—Ala—Cys—Ala—Ala—

20   21   22   23   24   25   26   27   28   29
    Asn—Cys—Leu—Ser—Leu—Gly—Lys—Ala—Gly—Gly—

30   31   32   33   34   35   36   37   38   39
    His—Cys—Glu—Lys—Gly—Val—Cys—Ile—Cys—Arg—

40   41   42   43   44   45   46   47   48   49
    Lys—Thr—Ser—Phe—Lys—Asp—Leu—Trp—Asp—Lys—

50   51
                                          Tyr—Phe—COOH
``` and a pharmaceutically acceptable carrier.

2. The antibacterial composition of claim 1 wherein the polypeptide has three intramolecular disulfide linkages at positions between 3 and 31, 17 and 36, and 21 and 38.

3. A method of treating Gram-positive bacteria comprising administering an antibacterially effective amount of isolated and purified polypeptide having the following amino acid sequence:

```
     1    2    3    4    5    6    7    8    9
NH2—Val—Thr—Cys—Asp—Leu—Leu—Ser—Phe—Lys—

10   11   12   13   14   15   16   17   18   19
    Gly—Gln—Val—Asn—Asp—Ser—Ala—Cys—Ala—Ala—

20   21   22   23   24   25   26   27   28   29
    Asn—Cys—Leu—Ser—Leu—Gly—Lys—Ala—Gly—Gly—

30   31   32   33   34   35   36   37   38   39
    His—Cys—Glu—Lys—Gly—Val—Cys—Ile—Cys—Arg—

40   41   42   43   44   45   46   47   48   49
    Lys—Thr—Ser—Phe—Lys—Asp—Leu—Trp—Asp—Lys—

50   51
                                          Tyr—Phe—COOH
``` thereby controlling Gram-positive bacteria.

4. The method of claim 3 wherein said polypeptide has three intramolecular disulfide linkages present at positions between 3 and 31, 17 and 36, and 21 and 38.

* * * * *